United States Patent
Eveland

(10) Patent No.: US 11,541,139 B2
(45) Date of Patent: Jan. 3, 2023

(54) APPARATUS AND METHOD FOR STERILIZING MATERIAL

(71) Applicant: American Sterilizer Company, Mentor, OH (US)

(72) Inventor: Randal W. Eveland, Kirtland, OH (US)

(73) Assignee: American Sterilizer Company, Mentor, OH (US)

( * ) Notice: Subject to any disclaimer, the term of this patent is extended or adjusted under 35 U.S.C. 154(b) by 333 days.

(21) Appl. No.: 16/562,516

(22) Filed: Sep. 6, 2019

(65) Prior Publication Data
US 2021/0069364 A1 Mar. 11, 2021

(51) Int. Cl.
| | |
|---|---|
| A61L 2/00 | (2006.01) |
| A61L 9/00 | (2006.01) |
| A61L 2/24 | (2006.01) |
| A61L 2/20 | (2006.01) |

(52) U.S. Cl.
CPC .............. *A61L 2/24* (2013.01); *A61L 2/0094* (2013.01); *A61L 2/208* (2013.01); *A61L 2202/11* (2013.01); *A61L 2202/122* (2013.01); *A61L 2202/13* (2013.01); *A61L 2202/24* (2013.01)

(58) Field of Classification Search
CPC .......... A61L 2/00; A61L 2/0094; A61L 2/208; A61L 2202/14; A61L 2202/24
USPC ................ 422/28, 32–33, 305, 307
See application file for complete search history.

(56) References Cited

U.S. PATENT DOCUMENTS

| | | | |
|---|---|---|---|
| 4,770,851 | A | 9/1988 | Joslyn |
| 4,952,370 | A | 8/1990 | Cummings et al. |
| 5,556,607 | A | 9/1996 | Childers et al. |
| 5,830,409 | A | 11/1998 | Childers et al. |
| 6,132,679 | A | 10/2000 | Conviser |

(Continued)

FOREIGN PATENT DOCUMENTS

| | | |
|---|---|---|
| CN | 202283362 U | 6/2012 |
| CN | 109125768 A | 1/2019 |

OTHER PUBLICATIONS

International Search Report and Written Opinion issued in corresponding International Application No. PCT/US2020/043993 dated Oct. 8, 2020.

(Continued)

*Primary Examiner* — Monzer R Chorbaji
(74) *Attorney, Agent, or Firm* — Kusner & Jaffe

(57) ABSTRACT

A method of sterilizing material includes receiving the material in a sterilizing chamber, vaporizing sterilant supplied to vaporizer from a sterilant source, exposing the material to the vaporized sterilant by conducting a sterilization cycle in the sterilizing chamber, heating ambient filtered air supplied to the vaporizer from an ambient filtered air source, and removing residuals of the vaporized sterilant absorbed or adsorbed by the material during the sterilization cycle by conducting an aeration cycle in the sterilizing chamber. The removing of the residuals includes conducting a plurality of aeration pulses to provide the sterilizing chamber with an aeration atmosphere comprising the heated filtered air to vaporize the absorbed or adsorbed residuals, and conducting a plurality of aeration vacuum pulses to evacuate the aeration atmosphere and vaporized residuals from the sterilizing chamber.

24 Claims, 4 Drawing Sheets

(56) References Cited

U.S. PATENT DOCUMENTS

| | | |
|---|---|---|
| 6,228,324 B1 | 5/2001 | Hasegawa et al. |
| 7,354,551 B2 | 4/2008 | Mielnik et al. |
| 8,962,707 B2 | 2/2015 | Singh |
| 9,302,021 B2 | 4/2016 | Klobusnik |
| 9,522,202 B1 | 12/2016 | Ahiska et al. |
| 2010/0313441 A1 | 12/2010 | McLaren et al. |
| 2013/0004380 A1* | 1/2013 | Yoo .................. A61L 2/208 |
| | | 422/186 |

OTHER PUBLICATIONS

PCT Written Opinion of the International Preliminary Examining Authority issued in related International Application No. PCT/US2020/043993 dated Jul. 14, 2021.

PCT International Preliminary Report on Patentability of the International Preliminary Examining Authority issued in related International Application No. PCT/US2020/043993 dated Dec. 2, 2021.

* cited by examiner

APPARATUS AND METHOD FOR STERILIZING MATERIAL

FIELD OF THE INVENTION

The present invention relates generally to sterilization of material and, more particularly, to a method of sterilizing and aerating material by respectively exposing the material to a sterilization atmosphere of vaporized sterilant and an aeration atmosphere of heated filtered air.

BACKGROUND OF THE INVENTION

Low-temperature sterilization methods, such as those incorporating the use of gaseous hydrogen peroxide, hydrogen peroxide gas plasma, ozone, peracetic acid, $NO_2$ gas, formaldehyde, and hydrogen peroxide with ozone, can be performed in sterilization chambers specifically designed for sterilization of material positioned within the chambers. Such methods commonly include a conditioning cycle for conditioning material prior to sterilization, a sterilization cycle that follows the conditioning cycle and sterilizes the material with sterilant, and an aeration cycle that removes sterilant that the materials have absorbed or adsorbed during the sterilization cycle.

An example sterilization cycle is illustrated in FIG. 1. The illustrated sterilization cycle includes a plurality of sterilization sets (pulses). While the example sterilization cycle illustrated in FIG. 1 includes four sterilization sets, embodiments described herein are not limited hereto. The sterilization sets (pulses) in a sterilization cycle may number less or greater than four, depending on how many sets (pulses) are needed in order to satisfactorily sterilize the material positioned within the sterilizing chamber. A pre-pulse injection may or may not be used.

Before the sterilization cycle is initiated, the conditioning cycle is performed. Specifically, the conditioning cycle is designed to prepare the materials for the sterilization cycle. This preparation is typically accomplished through the heating of the materials to remove any residual moisture, as some low temperature sterilization methods require the load to be thoroughly dried prior to sterilization.

Each of the sterilization sets (pulses) illustrated in FIG. 1 includes one or more sterilization pulses 32 and one or more vacuum pulses 30. Sterilization pulses 32 provide a sterilizing chamber with a sterilization atmosphere including a vaporized or gaseous sterilant. Vacuum pulses 30 evacuate the provided sterilization atmosphere from the sterilizing chamber.

During each sterilization pulse 32, a predetermined amount of vaporized or gaseous sterilant is provided into the sterilizing chamber containing the materials to be sterilized under vacuum. As a result, the pressure in the sterilizing chamber increases to a pressure greater than the initial pressure in the sterilizing chamber. The vaporized or gaseous sterilant is allowed to distribute itself through the sterilizing chamber for a period. A compression gas is then introduced into the closed chamber in an amount effective to raise the pressure in the chamber (sometime called a transition) to a sub-atmospheric or atmospheric pressure to drive the vaporized sterilant into lumens or passageways of the materials to be sterilized. This can be referred to as a transition. After the introduction of the compression gas and the provision of the vaporized sterilant into the sterilizing chamber, in vacuum pulses 30, the vaporized sterilant atmosphere is removed from the sterilizing chamber and destroyed, thereby ending the sterilization set. Then, either an additional sterilization set is executed or the sterilization cycle ceases.

After the sterilization cycle is complete, due to the desired driving of the vaporized sterilant into the target material, a significant amount of the vaporized sterilant may be absorbed or adsorbed by the material. The aeration cycle is used to remediate sterilant residues absorbed or adsorbed by sterilized materials to non-toxic levels.

A variety of specific aeration methods have been used to remove absorbed or adsorbed sterilant from medical devices on which sterilization cycles have been performed. Generally, the aeration cycle uses heated air pulses to vaporize or remove the absorbed or adsorbed sterilant residuals from the sterilized material and into the heated air atmosphere existing in the sterilizing chamber during aeration. The aeration atmosphere containing the vaporized sterilant residuals is subsequently removed from the sterilizing chamber, and the vaporized sterilant residuals in the aeration atmosphere are destroyed by a destroyer unit.

While research has shown that certain materials exposed to vaporized hydrogen peroxide have tended to retain higher levels of sterilant residuals, conventional sterilization processes have generally been satisfactorily in processing such worst-case scenarios. However, there is a desire in many industries, such as those related to medical device technology, to produce products using new materials that are even more absorptive to hydrogen peroxide. Such new materials are being contemplated for incorporation into single use or reusable medical devices. Further, some known materials as being used in processes, such as additive manufacturing technology and 3-D printing, that result in devices that are open to a greater degree and have greater surface areas. Conventional aeration methods are not sufficient to timely aerate such next-generation devices manufactured with new materials or methods.

For example, many conventional sterilization units employ the use of a jacket heater installed around the outer wall of the sterilization unit. The jacket heater is used to maintain the temperature of the atmosphere in the sterilizing chamber. During a sterilization cycle, the heat in the jacket heater is conducted through the outer wall of the sterilizing chamber and serves to maintain the vaporized state of the sterilant therein. During an aeration cycle, the heat in the jacket heater is also conducted through the outer wall of the sterilizing chamber in an attempt to heat the atmosphere within the sterilizing chamber at the time.

However, while the sterilant provided to the sterilizing chamber is a vapor state upon entering the sterilizing chamber, the atmosphere provided to the sterilizing chamber during the aeration cycle is ambient upon entering the sterilizing chamber. To adequately aerate the sterilizing chamber, both the aeration atmosphere and the materials being sterilized in the sterilization chamber must be at a temperature that is elevated above ambient temperature. Further, the jacket heater is typically the only source of heat provided to the aeration atmosphere. At reduced pressure, chamber air is not an efficient heat transfer medium.

As a result, upon entry to the sterilizing chamber, the ambient aeration atmosphere will have limited effectiveness in achieving or maintaining the necessary temperature of the surfaces of sterilized materials so that adsorbed or absorbed sterilant residuals can be vaporized from the surfaces. In addition, when the aeration atmosphere is evacuated, as adsorbed or absorbed residue is vaporized (an endothermic process to the materials), the heat provided by the aeration atmosphere is evacuated. This lowers the temperature of the material surfaces, as the vacuum established within the sterilizing chamber by the evacuation of the aeration atmosphere leaves no means by which the heat from the jacket heater can reach the material surfaces.

As such, an appropriate and efficient aeration strategy is needed in order to address the new challenges in material sterilization that cannot be addressed using conventional technology. The present invention has been developed to address these and other issues by providing a new aeration method capable of efficiently aerating materials incorporated into conventional and next-generation devices without degradation of the performance or structure thereof.

SUMMARY OF THE INVENTION

In accordance with an embodiment of the present invention, there is provided an apparatus for sterilizing material. The apparatus includes a sterilizing chamber, a vaporizer, a vacuum, and a controller. The sterilizing chamber is configured to receive the material. The vaporizer is configured to vaporize sterilant supplied from a sterilant source and heat ambient filtered air supplied from an ambient filtered air source. The vacuum is configured to evacuate the sterilizing chamber. The controller is configured to conduct a sterilization cycle in the sterilizing chamber to expose the material to the vaporized sterilant and an aeration cycle in the sterilizing chamber to remove residuals of the vaporized sterilant absorbed or adsorbed by the material during the sterilization cycle. The controller is further configured to conduct a plurality of sterilization pulses and a plurality of sterilization vacuum pulses during the sterilization cycle and a plurality of aeration pulses and a plurality of aeration vacuum pulses during the aeration cycle. Each of the sterilization pulses is conducted by the controller to provide the sterilizing chamber with a sterilization atmosphere including the vaporized sterilant. Each of the sterilization vacuum pulses is conducted by the controller to evacuate the provided sterilization atmosphere from the sterilizing chamber. Each of the aeration pulses is conducted by the controller to provide the sterilizing chamber with an aeration atmosphere comprising the heated filtered air to vaporize the absorbed or adsorbed residuals into the provided aeration atmosphere. Each of the aeration vacuum pulses is conducted by the controller to evacuate the provided aeration atmosphere including the vaporized residuals from the sterilizing chamber.

In accordance with an embodiment of the present invention, there is provided a method for sterilizing material. The method includes receiving the material in a sterilizing chamber, vaporizing sterilant supplied to vaporizer from a sterilant source, exposing the material to the vaporized sterilant by conducting a sterilization cycle in the sterilizing chamber, heating ambient filtered air supplied to the vaporizer from an ambient filtered air source, and removing residuals of the vaporized sterilant absorbed or adsorbed by the material during the sterilization cycle by conducting an aeration cycle in the sterilizing chamber. The exposing of the material includes conducting a plurality of sterilization pulses to provide the sterilizing chamber with a sterilization atmosphere comprising the vaporized sterilant, and conducting a plurality of sterilization vacuum pulses to evacuate the provided sterilization atmosphere from the sterilizing chamber. The removing of the residuals includes conducting a plurality of aeration pulses to provide the sterilizing chamber with an aeration atmosphere comprising the heated filtered air to vaporize the absorbed or adsorbed residuals, and conducting a plurality of aeration vacuum pulses to evacuate the provided aeration atmosphere including the vaporized residuals from the sterilizing chamber.

The present invention provides a new aeration approach that efficiently aerates and removes residual sterilant from highly absorptive materials incorporated into conventional and next-generation devices without any performance or structure degradation.

The new aeration approach can be especially implemented for the removal of residual hydrogen peroxide sterilant from highly absorptive materials.

The new aeration approach can also be implemented for the removal of residual hydrogen peroxide sterilant from additive manufacturing devices and 3-D printed devices, such, as for example, surgical models, surgical guides, and reusable medical instruments.

These and other advantages will become apparent from the following description of a preferred embodiment taken together with the accompanying drawings and claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
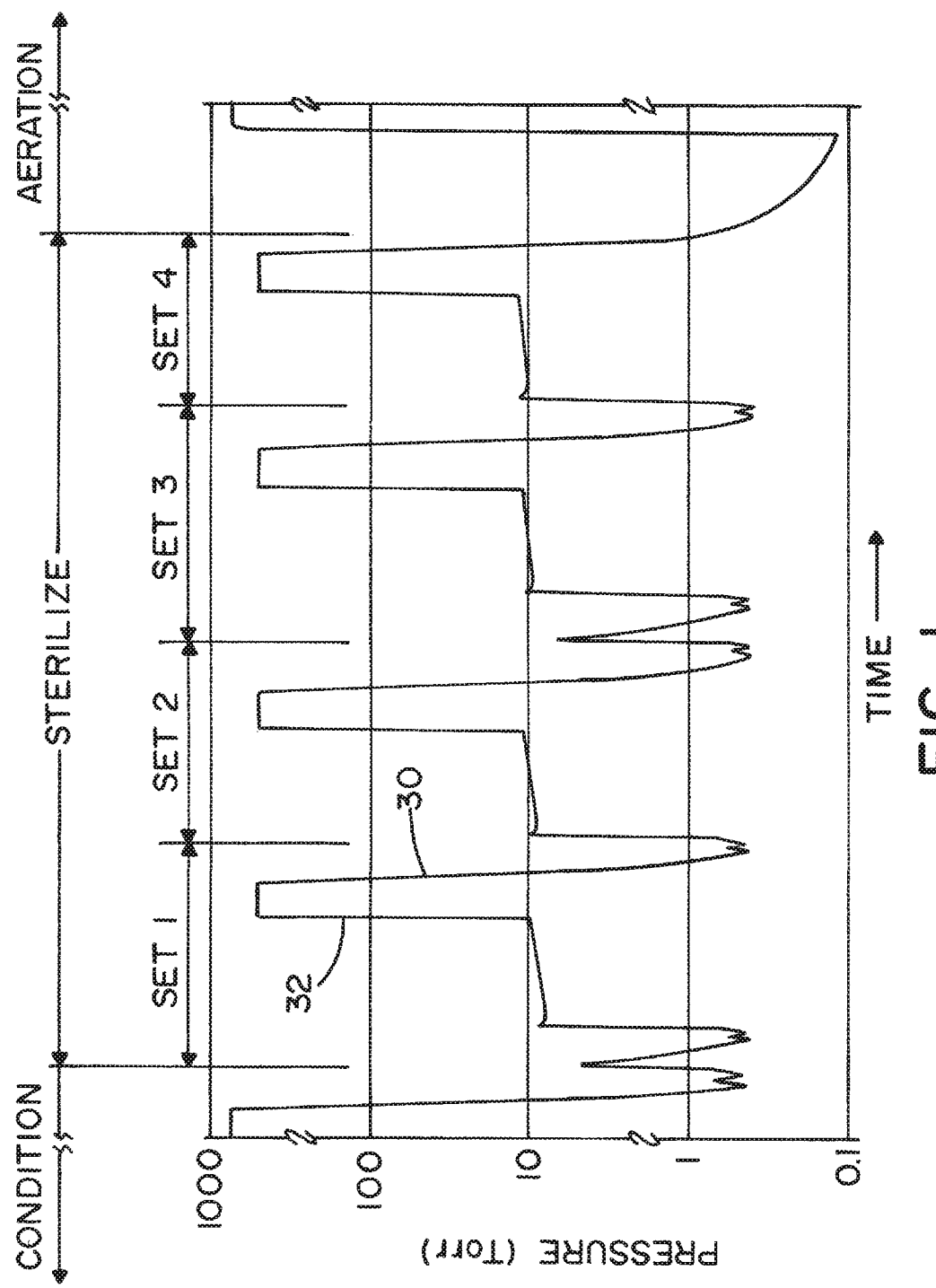
FIG. 1 is a pressure/time graph illustrating an example sterilization cycle of a method for sterilizing material of the present invention.
Figure 2:
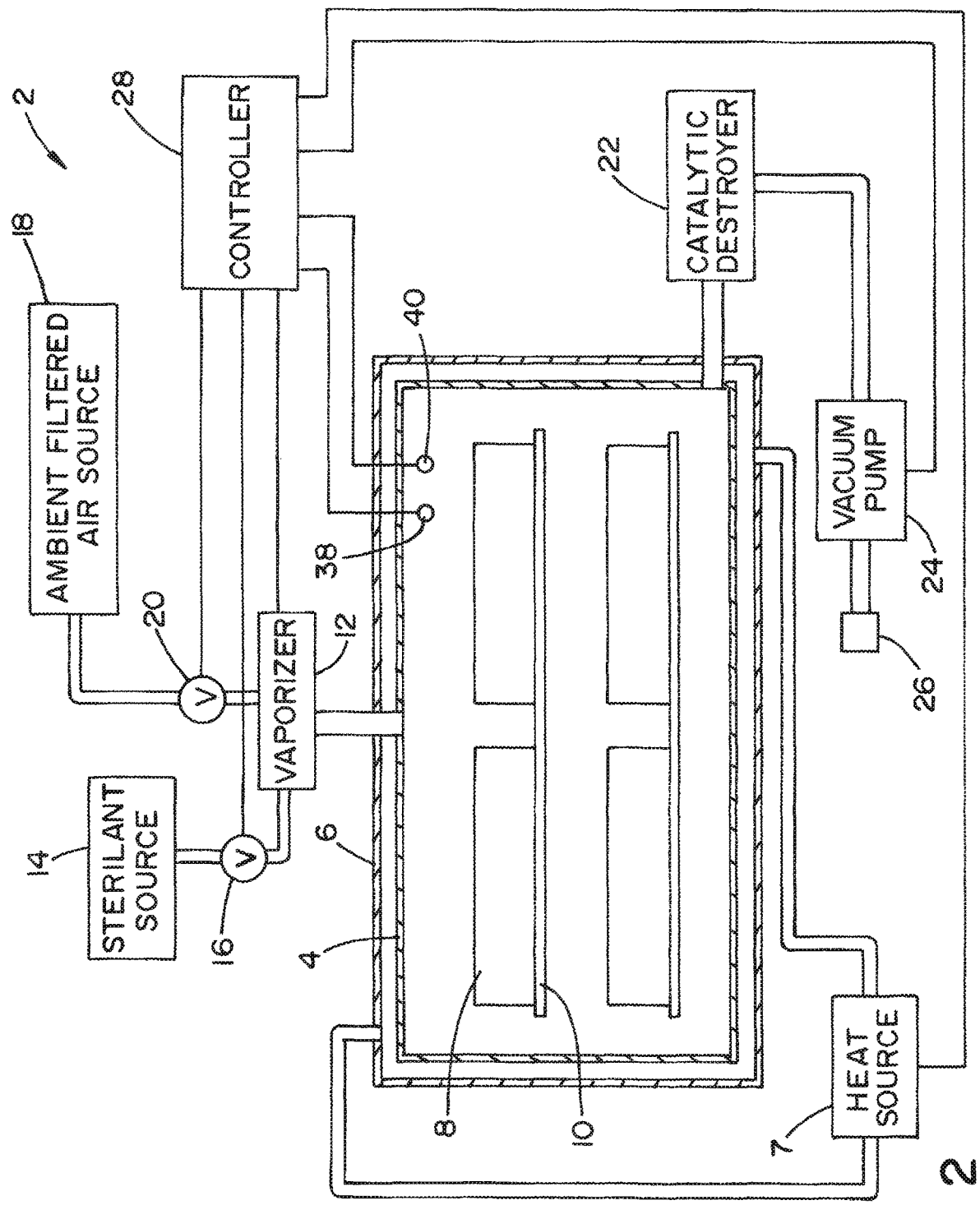
FIG. 2 is a schematic view illustrating an example apparatus for sterilizing material of the present invention.
Figure 4:
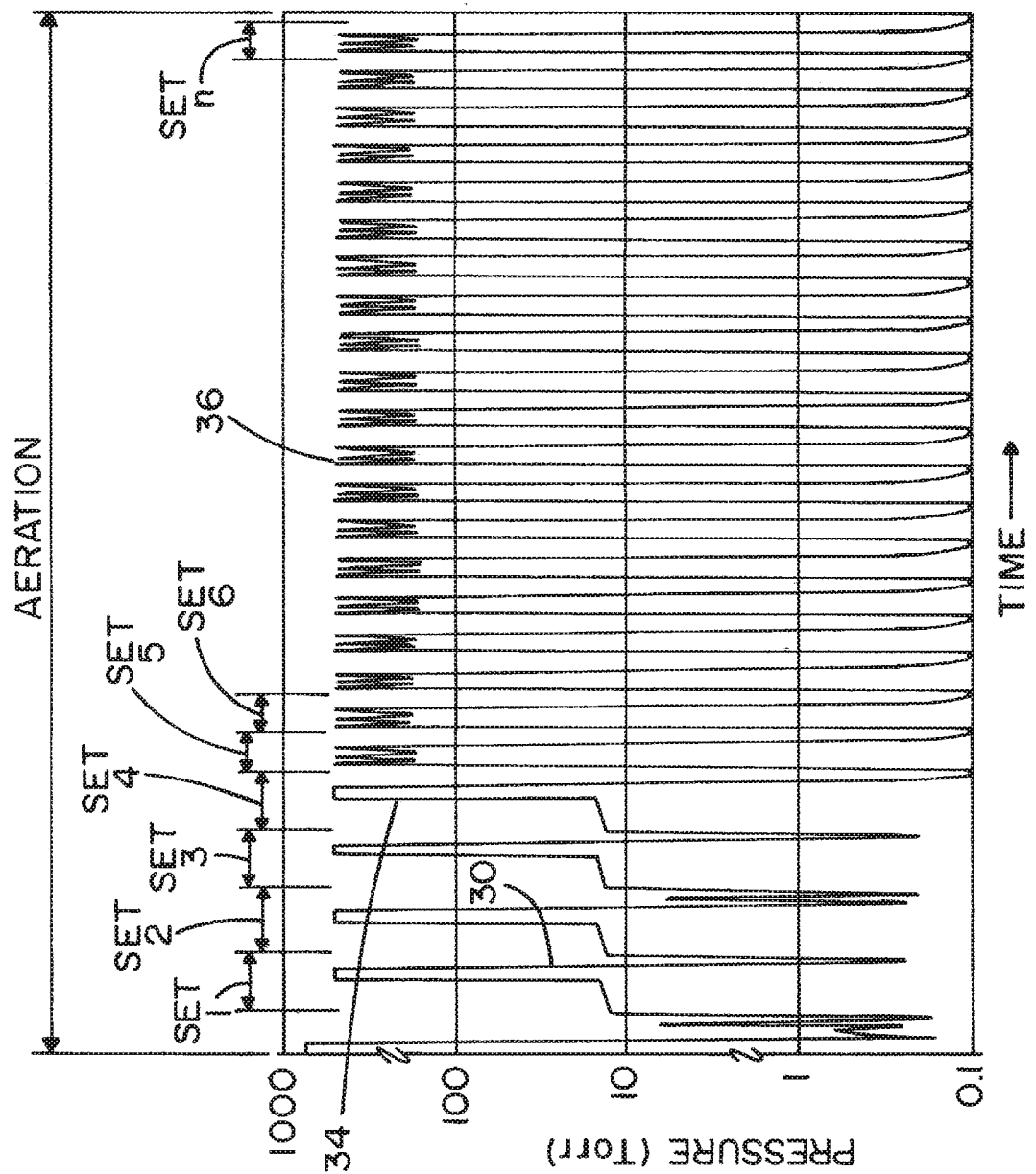
FIG. 4 is a pressure/time graph illustrating an example aeration/conditioning cycle of a method for sterilizing material of the present invention.

Referring now to the drawings, wherein the showing is for illustrating a preferred embodiment of the invention only and not for limiting same, the invention will be described with reference to FIGS. 2 and 4. FIG. 2 illustrates sterilizing apparatus 2 for sterilizing materials 8 placed in sterilizing chamber 4 of sterilizing apparatus 2. FIG. 4 illustrates a filtered air compression aeration cycle taking place within sterilizing chamber 4 for aerating sterilized materials 8 placed therein. FIG. 4 specifically illustrates the pressure within sterilizing chamber 4 over time of the aeration cycle.

Sterilizing apparatus 2 includes sterilizing chamber 4, vaporizer 12, sterilant source 14, sterilant source valve 16, ambient filtered air source 18, ambient filtered air source valve 20, a vacuum apparatus, and controller 28. Sterilizing chamber 4 receives materials 8 for sterilization thereof. In an example, sterilizing chamber 4 includes chamber shelves 10 on which materials 8 can be placed for easy handling thereof. Materials 8 may be packed in appropriate packaging for sterilization when loaded in sterilizing chamber 4, including, but not limited to, Tyvek® pouches or sterilization wrap.

Vaporizer 12 heats substances transferred therethrough. In the present example, vaporizer 12 vaporizes sterilant when the sterilant is allowed by sterilant source valve 16 to flow from sterilant source 14 to vaporizer. In addition, vaporizer 12 heats ambient filtered air when the ambient filtered air is allowed by ambient filtered air valve 20 to flow from ambient filtered air source 18 to vaporizer 12. The vaporized sterilant and the heated filtered air will be provided to sterilizing chamber 4 according to whether a conditioning cycle, a sterilization cycle, or an aeration cycle is taking place within sterilizing chamber 4. Valves 18 and 20 control whether vaporized sterilant or heated filtered air is provided to sterilizing chamber 4.

The sterilant provided by sterilant source 14 may be, in one example, liquid hydrogen peroxide. However, embodiments are not limited thereto, as other sterilant known by those having ordinary skill in the art to be similar to liquid hydrogen peroxide may be used.

Sterilizing chamber 4 is built according to standards enabling the use thereof with the vacuum apparatus, which includes catalytic destroyer 22, vacuum pump 24, and vacuum pump exhaust 26. While sterilizing apparatus 2 is in operation, the vacuum apparatus, specifically vacuum pump 24, evacuates atmospheres existing within sterilizing chamber 4. In an example, when sterilizing apparatus 2 is in operation, vacuum pump 24 is continuously evacuating the atmospheres existing within sterilizing chamber 4.

The atmospheres evacuated from sterilizing chamber 4 initially pass through catalytic destroyer 22, which breaks down all of the sterilant existing in the evacuated atmosphere into water and oxygen. After the sterilant destruction, the remnants of the evacuated atmosphere are exhausted through vacuum pump exhaust 26 to ambient air.

In addition, sterilizing apparatus 2 may include heating means 6 and heat source 7 for heating means 6. Heating means 6 may be one of several known systems known to be able to heat the outer wall of sterilizing chamber 4. In one example, heating means 6 may be a jacket heater surrounding the outer wall of sterilizing chamber 4. In this case, heat source 7 is an external heating system that transfers heat to a medium, which is then circulated through the jacket heater surrounding the outer wall of sterilizing chamber 4. The heat transfer medium may be steam, but is not limited thereto. The outer wall of sterilizing chamber 4 conducts the heat created by the heat transfer medium in the jacket heater through the outer wall of sterilizing chamber 4 to whatever atmosphere exists at the time within sterilizing chamber 4. The heat transfer medium is recycled from the jacket heater for further heating by heat source 7.

In another example, heating means 6 may be a plurality of resistive heating bands applied to the outer wall of sterilizing chamber 4. In this case, heat source 7 may be an external power source for powering the resistive heating bands. While the resistive heating bands can be positioned to surround the outer wall of sterilizing chamber 4, as is the case with the jacket heater, such positioning is not necessary.

Controller 28 is provided to control all aspects of sterilizing apparatus 2. For example, controller 28 is linked to each operational component of sterilizing apparatus 2 to enable the control thereof by controller 28. When an atmosphere of vaporized sterilant is desired in sterilizing chamber 4, controller 28 opens sterilant source valve 16 to allow liquid sterilant to be transferred from sterilant source 14 to vaporizer 12 for vaporization thereof. Controller 28 opens and closes sterilant source valve 16 in order to respectively allow sterilization pulses 32 and vacuum pulses 30 to occur during a sterilization cycle.

When an aeration atmosphere is desired in sterilizing chamber 4, controller 28 opens ambient filtered air source valve 20 to allow ambient filtered air to be transferred from ambient filtered air source 18 to vaporizer 12 for heating thereof. Controller 28 opens and closes ambient filtered air source valve 20 in order to respectively allow aeration pulses 32 and vacuum pulses 30. In one embodiment, after providing an aeration pulse 32 to sterilizing chamber 4 and prior to providing a vacuum pulse 30 to sterilizing chamber 4, controller 28 may conduct one or more aeration washes 36 by quickly opening and closing ambient filtered air source valve 20 to provide multiple short pulses of ambient filtered air to vaporizer 12. These aeration washes 36 serve as mechanisms by which sterilant residuals can be scrubbed and vaporized from materials 8.

Controller 28 may also be used to control the heating by heat source 7 of the heat transfer medium to enable conduction to occur from jacket heater 6 to sterilizing chamber 4 through the outer wall of sterilizing chamber 4. Controller 28 may further control operation of vaporizer 12 and vacuum pump 24, including, but not limited to, a temperature of vaporizer 12 and a vacuum force provided by vacuum pump 24.

Controller 28 is also linked to low-pressure transducer 38 and high-pressure transducer 40 in sterilizing chamber 4. Transducers 38 and 40 provide controller 28 with information as to the amount of pressure that exists in sterilizing chamber 4. This information enables controller 28 to operate the sterilization process according to a pressure and time program. An example of such a program is illustrated in FIG. 4 according to the pressure/time graph that illustrates an example aeration/conditioning cycle. This will be discussed in more detail below.

Figure 3:
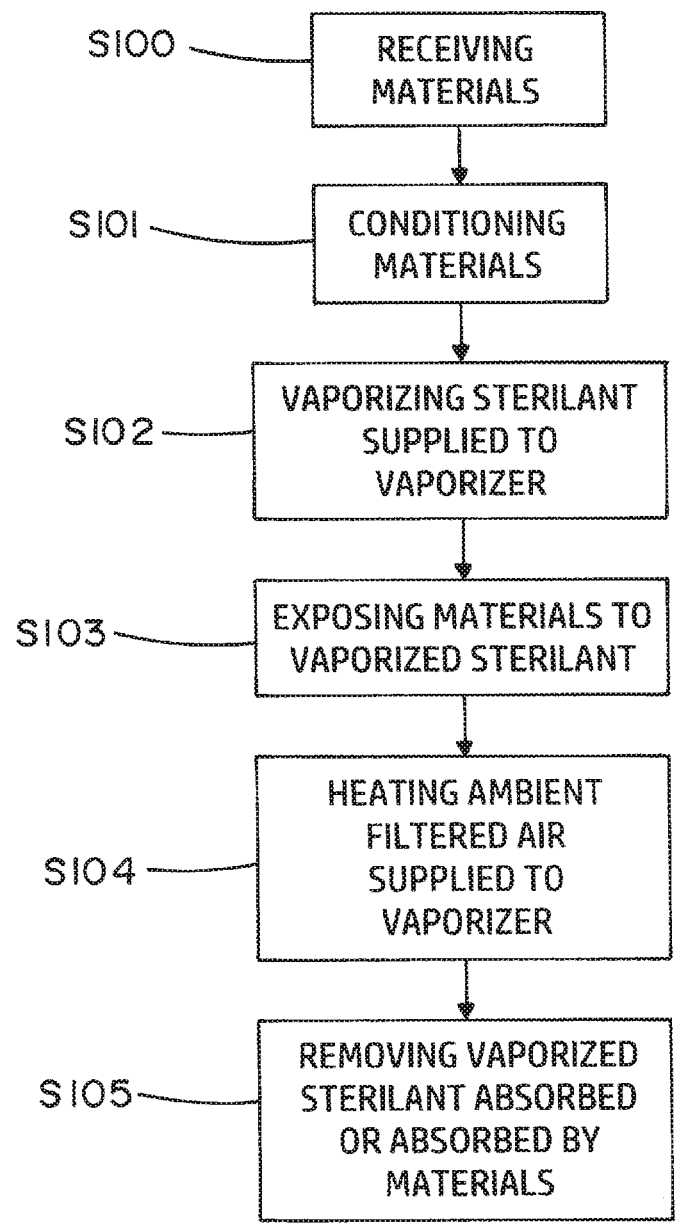
FIG. 3 is a flowchart illustrating an example method for sterilizing material of the present invention.

FIG. 3 illustrates an embodiment of the invention directed to a method of sterilizing materials 8 in sterilizing apparatus 2. Initially, materials 8 are received (S100) in sterilizing chamber 4. Materials 8 may then be conditioned (S101) within sterilizing chamber 4 using a conditioning cycle in preparation for a sterilization cycle. Conditioning (S101) will be discussed in more detail below.

Once materials 8 are deemed to be adequately conditioned, the conditioning cycle ends with a vacuum pulse 30 that evacuates the sterilization atmosphere from sterilizing chamber 4 to a pressure typically less than or equal to 40 Torr. Then, sterilant supplied to vaporizer 12 from sterilant source 14 is vaporized (S102). More specifically, controller 28 opens sterilant source valve 16, thereby permitting liquid sterilant to flow from sterilant source 14 to vaporizer 12, in which the liquid sterilant is vaporized (S102).

Materials 8 are then exposed (S103) to the vaporized sterilant as controller 28 conducts a sterilization cycle in sterilizing chamber 4. More specifically, controller 28 performs a plurality of sterilization sets within the sterilization cycle. Each sterilization set includes one or more sterilization pulses 32 and one or more vacuum pulses 30. Sterilization pulses 32 are conducted by controller 28 to provide sterilizing chamber 4 with a sterilization atmosphere including the vaporized sterilant. Controller 28 may accomplish this by opening sterilant source valve 16 to supply a predetermined amount of liquid sterilant to vaporizer 12, operating vaporizer 12 to vaporize the liquid sterilant provided through sterilant source valve 16 from sterilant source 14, and operating vacuum pump 24 to introduce a sterilization atmosphere including a predetermined amount of vaporized sterilant into sterilizing chamber 4. The amount of liquid sterilant supplied to vaporizer 12 is generally based on the side of sterilizing chamber 4. Sterilant may be introduced to ensure condensing or non-condensing conditions or, alternatively, be introduced to reach and maintain sterilization parameters, such as, but not limited to, pressure, sterilant concentration, or humidity.

After a sterilization pulse 32 is completed in a sterilization set, vacuum pulses 30 of the sterilization cycle are conducted by controller 28 to remove the remaining sterilization atmosphere from sterilizing chamber 4 such that a vacuum remains within sterilizing chamber 4. Controller 28 may accomplish this by closing sterilant source valve 16 and operating vacuum pump 24 to remove the sterilization atmosphere from sterilizing chamber 4, thereby leaving a vacuum in sterilizing chamber 4. At this point, sterilizing chamber 4 may be at a pressure between 0.1 and 1.0 Torr.

There are no limits on the amount of sterilization sets that can be performed in sterilizing chamber 4 during a sterilization cycle. The proper number of sterilization sets that should be conducted is fully dependent on the ability of the sterilization cycle to sterilize materials 8 with as few sterilization sets as necessary. Once materials 8 are deemed to be adequately sterilized, the sterilization cycle ends with a vacuum pulse 30 that evacuates the sterilization atmosphere from sterilizing chamber 4 to a pressure between 0.1 and 1.0 Torr.

An aeration cycle will now be featured with reference to FIGS. 3 and 4. After the sterilization cycle is complete and vacuum exists within sterilizing chamber 4, ambient filtered air supplied to vaporizer 12 from ambient filtered air source 18 is heated (S104). More specifically, controller 28 opens ambient filtered air source valve 20, thereby permitting ambient filtered air to flow from ambient filtered air source 18 to vaporizer 12, in which the ambient filtered air is heated (S104).

Vaporized sterilant residuals absorbed or adsorbed by materials 8 during the sterilization cycle are then removed (S105) by conducting the aeration cycle in sterilizing chamber 4. More specifically, controller 28 performs a plurality of aeration sets (Set 1, Set 2, . . . Set n) within the aeration cycle. Each aeration set includes one or more aeration pulses 34 and one or more vacuum pulses 30. Aeration pulses 34 are conducted by controller 28 to provide sterilizing chamber 4 with an aeration atmosphere including the heated filtered air. Controller 28 may accomplish this by opening of ambient filtered air source valve 20, operating vaporizer 12 to heat the ambient filtered air provided through ambient filtered air source valve 20 from ambient filtered air source 18, and operating vacuum pump 24 to introduce an aeration atmosphere including a predetermined amount of heated filtered air into sterilizing chamber 4. This raises the pressure in sterilizing chamber 4 to a pressure around 400 Torr.

After an aeration pulse 34 is completed in an aeration set, vacuum pulses 30 of the sterilization cycle are conducted by controller 28 to remove the remaining sterilization atmosphere from sterilizing chamber 4 such that a vacuum remains within sterilizing chamber 4. Controller 28 may accomplish this by closing sterilant source valve 16 and operating vacuum pump 24 to remove the sterilization atmosphere from sterilizing chamber 4, thereby leaving a vacuum in sterilizing chamber 4. At this point, sterilizing chamber 4 may be at a pressure between 0.1 and 1.0 Torr.

Within some of the aeration sets, the controller 28 may operate ambient filtered air source valve 20 to provide multiple short pulses of ambient filtered air to vaporizer 12, thereby resulting in aeration washes 36 being performed in sterilizing chamber 4. For example, in FIG. 4, each of sets 1-4 illustrates controller 28 opening ambient filtered air source valve 20 to increase pressure within sterilizing chamber 4 to a pressure around 400 Torr and operated ambient filtered air source valve 20 to maintain that pressure for a prolonged period. Then, controller 28 closes ambient filtered air source valve 20 for another prolonged period to evacuate sterilizing chamber 4.

Beginning with set 5, controller 28 opens ambient filtered air source valve 20 to increase pressure within sterilizing chamber 4 to a pressure around 400 Torr. However, controller 28 does not operate ambient filtered air source valve 20 to maintain the pressure around 400 Torr within sterilizing chamber 4 for a prolonged period. Instead, controller 28 immediately closes ambient filtered air source valve 20 after a pressure around 400 Torr in sterilizing chamber 4 is reached. Then, after a short period of evacuation within sterilizing chamber 4 to lower the pressure in sterilizing chamber 4 to around 150 Torr, controller 28 opens ambient filtered air source valve 20 to bring pressure in sterilizing chamber 4 back to around 400 Torr. This operation pattern of ambient filtered air source valve 20 is repeated several times, constituting an air wash 36. After air wash 36 is complete, controller 28 closes ambient filtered air source valve 20 for a prolonged period to completely evacuate sterilizing chamber 4 to a pressure between 0.1 and 1.0 Torr, thereby ending aeration set 5

In FIG. 4, the remainder of the sets following aeration set 5 includes air washes 36. However, embodiments are not limited thereto, as the aeration cycle is performed in a way that best serves to remove sterilant residue from materials 8. Indeed, there are no limits on the amount of aeration sets that can be performed in sterilizing chamber 4 during an aeration cycle. The proper number of aeration sets that should be conducted is fully dependent on the ability of the aeration cycle to materials 8 with as few aeration sets as necessary. Once materials 8 are deemed to be adequately aerated, the aeration cycle ends with a vacuum pulse 30 that evacuates the aeration atmosphere from sterilizing chamber 4 to a pressure between 0.1 and 1.0 Torr.

It is further noted that, while the conditioning (S101) occurs prior to the sterilization cycle in the vaporizing (S102) and the exposing (S103), in one example, the conditioning (S101) is performed in the way in which the heating (S104) and the removing (S105) is performed. In other words, the conditioning cycle may be operated in the same manner as is the aeration cycle. The heated filtered air provided to sterilizing chamber 4 during aeration can be used during conditioning to heat and prepare materials 8 to have vaporized sterilant driven therein, as vaporized sterilant can be more easily driven into heated materials 8 than materials 8 at ambient temperature.

While FIGS. 1-4 and the supporting disclosure illustrate the conditioning cycle, the sterilization cycle, and the aeration cycle as taking place within sterilizing chamber 4, embodiments described herein are not limited thereto. For example, an aerating chamber that is positioned separately from sterilizing chamber 4 may be used solely for the aeration cycle. In such an embodiment, vaporizer 12 is connected to the aerating chamber, and controller 28 is used to control the aeration cycle within the aerating chamber. The conditioning and sterilization cycles will continue to take place in sterilizing chamber 4. After the sterilization cycle is complete, sterilized materials 8 are transferred from sterilizing chamber 4 to the separate aerating chamber, in which sterilized materials 8 are aerated as previously described with respect to sterilizing chamber 4.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. An apparatus for sterilizing material, comprising:
a sterilizing chamber configured to receive the material;
a vaporizer to which an ambient filtered air source outside the sterilizing chamber is directly connected, the vaporizer being configured to vaporize sterilant supplied from a sterilant source and heat ambient filtered air supplied to the vaporizer from the ambient filtered air source;
a vacuum apparatus configured to evacuate the sterilizing chamber; and
a controller configured to conduct a sterilization cycle in the sterilizing chamber to expose the material to the vaporized sterilant and an aeration cycle in the sterilizing chamber to remove residuals of the vaporized sterilant absorbed or adsorbed by the material during the sterilization cycle, the controller being further configured to conduct a plurality of sterilization pulses and a plurality of sterilization vacuum pulses during the sterilization cycle and a plurality of aeration pulses and a plurality of aeration vacuum pulses during the aeration cycle, each of the sterilization pulses being conducted by the controller to provide the sterilizing chamber with a sterilization atmosphere comprising the vaporized sterilant, each of the sterilization vacuum pulses being conducted by the controller to evacuate the provided sterilization atmosphere from the sterilizing chamber, each of the aeration pulses being conducted by the controller to provide the sterilizing chamber with an aeration atmosphere comprising the heated filtered air to vaporize the absorbed or adsorbed residuals into the provided aeration atmosphere, each of the aeration vacuum pulses being conducted by the controller to evacuate the provided aeration atmosphere including the vaporized residuals from the sterilizing chamber.

2. The apparatus of claim 1, further comprising:
heating means for heating an outer wall of the sterilizing chamber, the heating means being configured to provide heat to the sterilizing chamber,
wherein the outer wall of the sterilizing chamber is configured to conduct the heat provided by the heating means therethrough to the provided sterilization atmosphere and the provided aeration atmosphere within the sterilizing chamber to respectively increase and maintain temperatures thereof, and
wherein the controller is further configured to operate the heating means to respectively increase and maintain a temperature of the provided sterilization atmosphere and the provided aeration atmosphere with the heat conducted through the outer wall of the sterilizing chamber.

3. The apparatus of claim 2, wherein the heating means comprises a jacket heater that surrounds the outer wall of the sterilizing chamber, and
wherein the heat is provided to the jacket heater through a medium that is heated externally by a heat source, circulated through the jacket heater, and recycled from the jacket heater for further heating by the heat source.

4. The apparatus of claim 2, wherein the heating means comprises a plurality of resistive heating bands that are powered by a power source.

5. The apparatus of claim 1, wherein the sterilant is hydrogen peroxide.

6. The apparatus of claim 1, wherein the controller is further configured to conduct a plurality of aeration sets within the aeration cycle, each of the aeration sets being conducted by the controller to include one or more of the aeration pulses and one or more of the aeration vacuum pulses, each of the aeration pulses comprising one or more aeration washes of the heated filtered air.

7. The apparatus of claim 6, wherein the controller is further configured to conduct the aeration washes at a pressure in a range from 100 Torr to 760 Torr.

8. The apparatus of claim 6, wherein the controller is further configured to conduct a conditioning cycle in the sterilizing chamber prior to conducting the sterilization cycle to condition the material for the sterilization cycle,
wherein the controller is further configured to conduct a plurality of conditioning pulses and a plurality of conditioning vacuum pulses during the conditioning cycle, each of the conditioning pulses being conducted by the controller to provide the sterilizing chamber with a conditioning atmosphere comprising the heated filtered air, each of the conditioning vacuum pulses being conducted by the controller to evacuate the provided conditioning atmosphere from the sterilizing chamber.

9. The apparatus of claim 8, wherein the aeration cycle conducted by the controller corresponds with the conditioning cycle conducted by the controller.

10. The apparatus of claim 8, wherein the aeration pulses conducted by the controller correspond with the conditioning pulses conducted by the controller.

11. The apparatus of claim 8, wherein the controller is further configured to conduct a plurality of conditioning sets within the conditioning cycle, each of the conditioning sets being conducted by the controller to include one or more of the conditioning pulses and one or more of the conditioning vacuum pulses, each of the conditioning pulses comprising one or more conditioning washes of the heated filtered air, and
wherein the aeration washes correspond with the conditioning washes.

12. The apparatus of claim 1, wherein the material includes one or more of medical devices and medical instruments.

13. A method for sterilizing material, comprising:
receiving the material in a sterilizing chamber;
vaporizing sterilant supplied to a vaporizer from a sterilant source;
exposing the material to the vaporized sterilant by conducting a sterilization cycle in the sterilizing chamber, the exposing of the material comprising:
conducting a plurality of sterilization pulses to provide the sterilizing chamber with a sterilization atmosphere comprising the vaporized sterilant; and
conducting a plurality of sterilization vacuum pulses to evacuate the provided sterilization atmosphere from the sterilizing chamber;
using the vaporizer to heat ambient filtered air supplied to the vaporizer from an ambient filtered air source that is located outside of the sterilizing chamber and directly connected to the vaporizer; and
removing residuals of the vaporized sterilant absorbed or adsorbed by the material during the sterilization cycle by conducting an aeration cycle in the sterilizing chamber, the removing of the residuals comprising:
conducting a plurality of aeration pulses to provide the sterilizing chamber with an aeration atmosphere comprising the heated filtered air to vaporize the absorbed or adsorbed residuals; and conducting a plurality of aeration vacuum pulses to evacuate the provided aeration atmosphere including the vaporized residuals from the sterilizing chamber.

14. The method of claim 13, further comprising:
providing heat to the sterilizing chamber by heating an outer wall of the sterilizing chamber via heating means; and
conducting the heat provided by the heating means through the outer wall of the sterilizing chamber to the provided sterilization atmosphere and the provided aeration atmosphere to respectively increase and maintain temperatures thereof.

15. The method of claim 14, wherein the heating means comprises a jacket heater that surrounds the outer wall of the sterilizing chamber; and
wherein the heat is provided to the jacket heater through a medium that is heated externally by a heat source, circulated through the jacket heater, and recycled from the jacket heater for further heating by the heat source.

16. The method of claim 14, wherein the heating means comprises a plurality of resistive heating bands that are powered by a power source.

17. The method of claim 13, wherein the sterilant is hydrogen peroxide.

18. The method of claim 13, further comprising:
conducting a plurality of aeration sets within the aeration cycle, each of the aeration sets including one or more of the aeration pulses and one or more of the aeration vacuum pulses,
wherein the conducting of the aeration pulses comprises conducting one or more aeration washes of the heated filtered air.

19. The method of claim 18, wherein the aeration washes are conducted at a pressure in a range from 100 Torr to 760 Torr.

20. The method of claim 18, further comprising:
conditioning the material for the sterilization cycle by conducting a conditioning cycle in the sterilizing chamber, the conditioning of the material comprising:
conducting a plurality of conditioning pulses to provide the sterilizing chamber with a conditioning atmosphere comprising the heated filtered air; and
conducting a plurality of conditioning vacuum pulses to evacuate the provided conditioning atmosphere from the sterilizing chamber.

21. The method of claim 20, wherein the aeration cycle corresponds with the conditioning cycle.

22. The method of claim 20, wherein the aeration pulses correspond with the conditioning pulses.

23. The method of claim 20, further comprising:
conducting a plurality of conditioning sets within the conditioning cycle, each of the conditioning sets including one or more of the conditioning pulses and one or more of the conditioning vacuum pulses,
wherein the conducting of the conditioning pulses comprises one or more conditioning washes of the heated filtered air, and
wherein the aeration washed correspond with the conditioning washes.

24. The method of claim 13, further comprising:
controlling the conducting of the sterilizing cycle and the conducting of the aeration cycle using a controller.

* * * * *